US009439891B2

(12) United States Patent
Roberts et al.

(10) Patent No.: US 9,439,891 B2
(45) Date of Patent: *Sep. 13, 2016

(54) METHODS FOR TREATING HYPERURICEMIA IN PATIENTS WITH GOUT USING HALOFENATE OR HALOFENIC ACID AND A SECOND URATE-LOWERING AGENT

(71) Applicant: CymaBay Therapeutics, Inc., Newark, CA (US)

(72) Inventors: Brian K. Roberts, Palo Alto, CA (US); Gopal Chandra Saha, Dublin, CA (US); Brian Edward Lavan, San Francisco, CA (US); Charles A. McWherter, Oakland, CA (US)

(73) Assignees: CymaBay Therapeutics, Inc., Newark, CA (US); DiaTex, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/667,145

(22) Filed: Mar. 24, 2015

(65) Prior Publication Data

US 2015/0258053 A1 Sep. 17, 2015

Related U.S. Application Data

(63) Continuation of application No. 13/668,164, filed on Nov. 2, 2012, now Pat. No. 9,023,856.

(60) Provisional application No. 61/555,920, filed on Nov. 4, 2011.

(51) Int. Cl.
| A61K 31/192 | (2006.01) |
| A61K 31/216 | (2006.01) |
| A61K 31/426 | (2006.01) |
| A61K 31/519 | (2006.01) |
| A61K 45/06 | (2006.01) |
| A61K 9/00 | (2006.01) |
| A61K 9/10 | (2006.01) |
| A61K 9/20 | (2006.01) |
| A61K 9/48 | (2006.01) |

(52) U.S. Cl.
CPC ............ *A61K 31/426* (2013.01); *A61K 9/0095* (2013.01); *A61K 9/10* (2013.01); *A61K 9/20* (2013.01); *A61K 9/48* (2013.01); *A61K 31/192* (2013.01); *A61K 31/216* (2013.01); *A61K 31/519* (2013.01); *A61K 45/06* (2013.01)

(58) Field of Classification Search
None
See application file for complete search history.

(56) References Cited

U.S. PATENT DOCUMENTS

| 3,517,050 | A | 6/1970 | Bolhofer et al. | |
| 4,250,191 | A | 2/1981 | Edwards | |
| 5,021,448 | A * | 6/1991 | Piraino ................. | A61K 31/44 514/385 |
| 5,057,427 | A | 10/1991 | Wald et al. | |
| 5,077,217 | A | 12/1991 | Matson et al. | |
| 6,262,118 | B1 | 7/2001 | Luskey et al. | |
| 6,613,802 | B1 * | 9/2003 | Luskey ............... | A61K 31/075 514/559 |
| 6,624,194 | B1 | 9/2003 | Luskey et al. | |
| 6,646,004 | B1 | 11/2003 | Luskey et al. | |
| 7,199,259 | B2 | 4/2007 | Daugs et al. | |
| 7,432,394 | B2 | 10/2008 | Cheng et al. | |
| 7,576,131 | B2 | 8/2009 | Luskey et al. | |
| 7,714,131 | B2 | 5/2010 | Zhu et al. | |
| 9,023,856 | B2 * | 5/2015 | Roberts ............... | A61K 31/519 514/262.1 |
| 2003/0220399 | A1 | 11/2003 | Luskey et al. | |
| 2010/0093854 | A1 | 4/2010 | Broggini et al. | |
| 2010/0137305 | A1 | 6/2010 | Davis | |
| 2010/0160351 | A1 * | 6/2010 | Jenkins ............... | A61K 31/167 514/262.1 |
| 2011/0268801 | A1 | 11/2011 | Quart et al. | |

FOREIGN PATENT DOCUMENTS

| WO | 2009/151695 A1 | 12/2009 |
| WO | 2011/032175 A1 | 3/2011 |

OTHER PUBLICATIONS

Hutchison et al. Atherosclerosis, Nov. 1973, vol. 18, No. 3, pp. 353-362.*
Becker et al. N. Engl. J. Med., Dec. 8, 2005, vol. 353, No. 23, pp. 2450-2461.*
Aronow et al., Curr. Ther. Res., v. 15, pp. 902-906 (1973).
Edwards, Cleveland Clinic. J. Med., v. 75, pp. S14-S16 (2008).
El-Zawawy et al., Cleveland Clinic J. Med., v. 77, pp. 919-927 (2010).
Higuchi et al., "Pro-Drugs as Novel Delivery Systems", v. 14, ACS Symposium Series (1975).
Keller et al., Arzneimittel-Forsch./Drug Research, v. 26(12), pp. 2221-2224 (1976) [Article in German, EMBASE English abstract].
Li et al., J. Pharmaceutical Sciences, v.86(10), pp. 1073-1088 (1997).

(Continued)

*Primary Examiner* — James D Anderson
(74) *Attorney, Agent, or Firm* — Sam L. Nguyen; Hamilton DeSanctis & Cha, LLP

(57) ABSTRACT

Disclosed herein are pharmaceutical compositions, methods and kits for lowering the serum uric acid level of a subject and for the treatment of a condition associated with elevated serum uric acid levels comprising administering a composition comprising a first urate-lowering agent and a second urate-lowering agent. In some aspects the first urate-lowering agent is (−)-halofenate, (−)-halofenic acid, or a pharmaceutically acceptable salts thereof. In some aspects the second urate-lowering agent is an inhibitor of uric acid production, a uricosuric agent, a uricase, or a pharmaceutically acceptable salt thereof.

16 Claims, No Drawings

(56) References Cited

OTHER PUBLICATIONS

Liu-Bryan et al., Arthritis Rheum., v. 52, pp. 2936-2946 (2005).
Lochmuller, Chromatography, v. 113, pp. 283-302 (1975).
Rautio et al., Nat. Rev. Drug Discov., v. 7, pp. 255-270 (2008).
Saha et al., Arthritis Rheum., v. 63(10), Suppl. S, p. S1014 (Oct. 2011).
Smith et al., J. Pain, v. 12(11), pp. 1113-1129 (Sep. 28, 2011).
Stockert et al., Clin. Med. Insights: Therapeutics, v. 2, pp. 927-945 (2010).
Tirosh et al., N. Engl. J. Med., v. 353, pp. 1454-1462 (2005).
Torres et al., Ann. Rheum. Dis., v. 68, pp. 1602-1608 (2009).
Whitehouse et al., Ann. N.Y. Acaad. Sci., v. 226(30), pp. 309-318 (1973).
Anonymous, NCT01399008 (Jul. 20, 2011), https://clinicaltrials.gov/archive/NCT01399008/2011_07_20.
Anonymous, NCT01416402 (Oct. 21, 2011), https://clinicaltrials.gov/archive/NCT01416402/2011_10_21.
Anonymous, Metabolex press release (May 19, 2011), http://www.prnewswire.com/news-releases.
Anonymous, Metabolex press release (Oct. 20, 2011), http://www.fiercebiotech.com.

* cited by examiner

METHODS FOR TREATING HYPERURICEMIA IN PATIENTS WITH GOUT USING HALOFENATE OR HALOFENIC ACID AND A SECOND URATE-LOWERING AGENT

CROSS-REFERENCE TO RELATED APPLICATIONS

This application is a continuation of U.S. application Ser. No. 13/668,164, filed on Nov. 2, 2012. Application Ser. No. 13/668,164 claims priority to U.S. Provisional Application No. 61/555,920, filed on Nov. 4, 2011, the complete disclosure of which is incorporated by reference herein.

BACKGROUND

Conditions associated with elevated serum uric acid levels (hyperuricemia) include disorders of urate crystal deposition such as gout arthropathy and tophi, urolithiasis (urinary tract stones), urate nephropathy, as well as the sequelae of these disorders. Hyperuricemia is associated with an increased risk of developing gout arthropathy, and the risk of gout increases with the degree and duration of the hyperuricemia. In addition to gout arthropathy, chronic hyperuricemia may lead to the deposition of uric acid crystals in the urinary tract, renal parenchyma, and soft tissues, resulting in urolithiasis, urate nephropathy with chronic kidney disease, and soft tissue tophi, respectively. Because of limitations and disadvantages of current uric acid lowering agents, more effective methods, compositions and therapies to lower uric acid are needed.

SUMMARY

In one embodiment, the present application describes methods of lowering the serum uric acid level of a subject with hyperuricemia, the method comprising administering to the subject a first urate-lowering agent and a second urate-lowering agent, wherein the first urate-lowering agent is a compound of Formula (I)

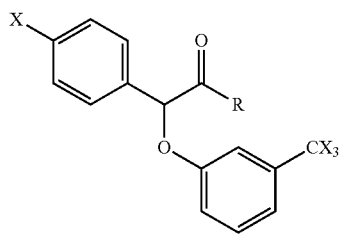

wherein R is selected from the group consisting of hydroxy, lower aralkoxy, di-lower alkylamino-lower alkoxy, lower alkanamido-lower alkoxy, benzamido-lower alkoxy, ureido-lower alkoxy, N'-lower alkyl-ureido-lower alkoxy, carbamoyl-lower alkoxy, halophenoxy-substituted lower alkoxy, carbamoyl-substituted phenoxy, carbonyl-lower alkylamino, N,N-di-lower alkylamino-lower alkylamino, halo-substituted lower alkylamino, hydroxyl-substituted lower alkylamino, lower alkanolyloxy-substituted lower alkylamino, ureido, and lower alkoxy carbonylamino; and each X is independently a halogen; or a pharmaceutically acceptable salt thereof.

Also disclosed are methods of treating a subject having a condition associated with hyperuricemia, the method comprising administering to the subject a first urate-lowering agent and a second urate-lowering agent, wherein the first urate-lowering agent is a compound of Formula (I). Also disclosed are methods of treating hyperuricemia in a subject with gout comprising administering to the subject a composition comprising a first urate-lowering agent and a second urate-lowering agent, wherein the first urate-lowering agent is a compound of Formula (I).

Also disclosed are compositions and kits comprising a first urate-lowering agent and a second urate-lowering agent, wherein the first urate-lowering agent is a compound of Formula (I).

In some aspects, the compound of Formula (I) is (−)-halofenate, (−)-halofenic acid, or a pharmaceutically acceptable salt thereof. In some aspects, the second urate-lowering agent is a xanthine oxidase inhibitor, an inhibitor of uric acid production, a uricosuric agent or a uricase. In some aspects, the second urate-lowering agent is allopurinol or febuxostat. Other aspects are provided below.

Currently available uric acid lowering agents and other therapeutic agents in development have limitations in their ability to lower serum uric acid to a desirable level, and their use may be limited by various adverse side effects or toxicities. For example, certain agents including allopurinol and febuxostat, when used as the only urate-lowering agent to treat hyperurecimia and at commonly prescribed doses, often fail to reach the common therapeutic target of serum uric acid levels of 6 mg/dL or less. Advantages of the compositions, methods, and kits disclosed herein over currently available uric acid lowering agents at commonly prescribed doses and treatment methods using such agents may include improved therapeutic benefits; an additive or over-additive effect as compared to the effects of single-agent therapies; beneficial effects on other conditions associated with hyperuricemia and urate crystal deposition; and provoking fewer or less intense side effects. In some aspects, the synergistic effect allows dose reduction or dosing interval extension relative to a currently available uric acid lowering agent taken individually at prescribed doses.

DETAILED DESCRIPTION

As utilized in accordance with the present disclosure, the following terms, unless otherwise indicated, shall be understood to have the following meanings:

"About" when qualifying a number, refers to a range of plus or minus ten percent of that value or number, unless indicated otherwise. Without limiting the application of the doctrine of equivalents as to the scope of the claims, each number should be construed in light of such factors as the number of reported significant digits and the manner or method (e.g. instrumentation, sample preparation, etc.) used to obtain that number.

"Administering" or "administration" refers to the act of giving a drug, prodrug, or therapeutic agent to a subject. Exemplary routes of administration are discussed below.

"Acute gout" refers to gout present in a subject with at least one gouty symptom (e.g., podagra or other gouty arthritis, gout flare, gouty attack).

"Arhalofenate" refers to (−)-halofenate, i.e. (−)-(R)-(4-chloro-phenyl)-(3-trifluoromethyl-phenoxy)-acetic acid 2-acetylamino-ethyl ester.

"Chronic gout" refers to gout present in a subject having recurrent or prolonged gout flares, tophus formation, chronic inflammatory arthritis, or joint deterioration associated with gout, and includes the periods following recovery from acute gout and between acute gout attacks (i.e. intercritical gout).

"Composition" or, interchangeably, "formulation" refers to a preparation that contains a mixture of various excipients and key ingredients that provide a relatively stable, desirable, and useful form of a compound or drug.

The prefixes "d" and "l" or (+) and (−) are employed to designate the sign of rotation of plane-polarized light by the compound, with (+) or d—meaning that the compound is "dextrorotatory" and with (−) or l—meaning that the compound is "levorotatory". For a given chemical structure, these isomers or "optical isomers" are identical except that they are mirror images of one another. In describing an optically active compound, the prefixes R and S are used to denote the absolute configuration of the molecule about its chiral center(s). There is no correlation between the nomenclature for the absolute stereochemistry and for the rotation of an enantiomer (i.e., the R-isomer can also be the l—isomer). A specific optical isomer can also be referred to as an "enantiomer," and a mixture of such isomers is often called an "enantiomeric" or "racemic" mixture. See, e.g., A. Streitwiesser, & C. H. Heathcock, INTRODUCTION TO ORGANIC CHEMISTRY, $2^{nd}$ Edition, Chapter 7 (MacMillan Publishing Co., U.S.A. 1981). The optical rotation $[\alpha]_D$ of (−)-halofenate was measured in methyl alcohol.

"Elevated serum uric acid level" refers to a serum uric acid level greater than normal and, in patients with gout, generally refers to a serum uric acid level greater than or equal to about 6 mg/dL. In some instances, elevated serum uric acid levels are above the mean level in a given population, such as those of a particular gender or age.

"Effective amount" refers to an amount required (i) at least partly to attain the desired response in a subject; (ii) to delay or to prevent the onset of a particular condition being treated in a subject; or (iii) or to inhibit or to prevent the progression of a particular condition being treated in a subject. The effective amount for a particular subject varies depending upon the health and physical condition of the subject to be treated, the taxonomic group of individual to be treated, the degree of protection desired, the formulation of the composition, the assessment of the medical situation, and other relevant factors. It is expected that the amount will fall in a relatively broad range that can be determined through routine trials.

"First urate-lowering agent" refers to a compound of any of Formula (I), (II), (III) or (IV) or a therapeutically acceptable salt or prodrug thereof.

"Gout" refers to a group of disorders or symptoms most often associated with the buildup of uric acid due to an overproduction of uric acid or a reduced ability of the kidney to excrete uric acid. Gout is often characterized by the deposition of urate crystals (uric acid or salts thereof, e.g. monosodium urate) in the joints (gouty arthropathy) or soft tissue (tophi). "Gout" as used herein includes acute gout, chronic gout, moderate gout, refractory gout and severe gout.

"Gout-associated inflammation" refers to local or systemic inflammation due to immune responses to the deposition of urate crystals.

"Halofenate" refers to the compound of Formula (III), i.e. (4-chlorophenyl)-(3-trifluoromethylphenoxy)-acetic acid 2-acetylaminoethyl ester (also referred to as the 2-acetamidoethyl ester of 4-chlorophenyl-(3-trifluoromethylphenoxy)-acetic acid. The term halofenate and the corresponding chemical names include both the (+) and (−) enantiomer of compounds of Formula (III) as well as mixtures thereof, unless otherwise specified.

"Halofenic acid" and "CPTA" refer to the compound of Formula (IV), i.e. 4-chlorophenyl-(3-trifluoromethylphenoxy)-acetic acid [also referred to as 2-(4-chlorophenyl)-2-(3-(trifluoromethyl)phenoxy)acetic acid] as well as its pharmaceutically acceptable salts. The term halofenic acid and the corresponding chemical names include both the (+) and (−) enantiomer of compounds of Formula (II) as well as mixtures thereof, unless otherwise specified.

"Hyperuricemia" refers to an elevated serum uric acid level (see above).

"Lower," when used to describe chemical substituents of compounds of Formulae (I) and (II) such as lower aralkoxy, di-lower alkylamino-lower alkoxy, lower alkanamido, lower alkoxy, benzamido-lower alkoxy, ureido-lower alkoxy, N'-lower alkyl-ureido-lower alkoxy, carbamoyl-lower alkoxy, halophenoxy substituted lower alkoxy, carbonyl-lower alkylamino, N,N-di-lower alkylamino-lower alkylamino, halo substituted lower alkylamino, hydroxy substituted lower alkylamino, lower alkanolyloxy substituted lower alkylamino, lower alkoxycarbonylamino, phenyl-lower alkyl, lower alkanamido-lower alkyl, and benzamido-lower alkyl refers to groups having from one to six carbon atoms. For example, "lower alkoxy" means $C_{1-6}$ alkoxy.

"Moderate gout" refers to gout present in a subject having at least two gout flares in the past 12 months.

"Pharmaceutically acceptable" refers to that which is useful in preparing a pharmaceutical composition that is generally safe, non-toxic, and neither biologically nor otherwise undesirable, and includes that which is acceptable for veterinary or human pharmaceutical use.

"Pharmaceutically acceptable salt" includes pharmaceutically acceptable acid addition salts and pharmaceutically acceptable base addition salts and includes both solvated and unsolvated forms. Representative non-limiting lists of pharmaceutically acceptable salts can be found in S. M. Berge et al., *J. Pharma Sci.*, 66(1), 1-19 (1977), and *Remington: The Science and Practice of Pharmacy*, R. Hendrickson, ed., 21st edition, Lippincott, Williams & Wilkins, Philadelphia, Pa., (2005), at p. 732, Table 38-5, both of which are hereby incorporated by reference herein.

"Pharmaceutically acceptable acid addition salt" refers to salts formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to salts prepared from the addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

"Refractory gout" refers to gout in patients who are unresponsive or poorly responsive, or have experienced or are at an increased risk of experiencing an adverse event, after being administered either (1) one or more second urate-lowering agents but not a first urate-lowering agent or (2) a first-urate lowering agent but not a second urate-lowering agent. The terms "unresponsive" and "poorly responsive" in this context include (1) no or insignificant lowering of serum uric acid, (2) failure to reach a target serum uric acid level (e.g. as determined by a physician or other medical practitioner), and (3) the persistence of one or more gouty conditions or symptoms such as gout flares, gouty tophus, gouty arthritis, or other associated conditions regardless of any lowering of serum uric acid levels.

"Second urate-lowering agent" refers to a therapeutic agent that lowers serum uric acid levels that is not a first urate-lowering agent. Second urate-lowering agents include currently available agents (i.e. an agent approved by the FDA or other appropriate regulatory authority as of the filing date of this application) that lower serum uric acid, as well as compounds currently in development or under regulatory review. Examples of second urate-lowering agents are provided below.

"Subject" and "patient" refer to animals such as mammals, including humans, other primates, domesticated animals (e.g. dogs, cats), farm animals (e.g. horses, cattle, goats, sheep, pigs), rats and mice.

"Severe gout" refers to gout present in a subject having tophaceous deposits in the joints, skin, or kidneys resulting in chronic arthritis, joint destruction, subcutaneous tophi, or kidney dysfunction, and, in some cases, with subsequent deformity and/or disability.

"Substantially free from" when used in reference to (−)-halofenate or (−)-halofenic acid (or a salt thereof) being substantially free from the corresponding (+) enantiomer (i.e. (+)-halofenate, (+)-halofenic acid, or a salt thereof) refers to a composition containing a high proportion of a compound's (−) enantiomer in relation to the (+) enantiomer. In one embodiment, the term means that by weight, the compound included in the composition is at least 85% (−) enantiomer and at most 15% (+) enantiomer. In one embodiment, the term means that by weight, the compound included in the composition is at least 90% (−) enantiomer and at most 10% (+) enantiomer. In other embodiments, the term means that by weight, the compound included in the composition is at least 91% (−) enantiomer and at most 9% (+) enantiomer, at least 92% (−) enantiomer and at most 8% (+) enantiomer, at least 93% (−) enantiomer and at most 7% (+) enantiomer, at least 94% (−) enantiomer and at most 6% (+) enantiomer, at least 95% (−) enantiomer and at most 5% (+) enantiomer, at least 96% (−) enantiomer and at most 4% (+) enantiomer, at least 97% (−) enantiomer and at most 3% (+) enantiomer, at least 98% (−) enantiomer and at most 2% (+) enantiomer, or at least 99% (−) enantiomer or greater than 99% (−) enantiomer. Other percentages of the (−) and (+) enantiomers may also be provided. These percentages are based upon the amount of the enantiomer relative to the total amount of both enantiomers of the compound in the composition.

"Therapeutically effective dose," "therapeutically effective amount," or, interchangeably, "pharmacologically acceptable dose" and "pharmacologically acceptable amount" mean that a sufficient amount of a therapeutic agent, therapeutic agents, or metabolites thereof will be present in order to achieve a desired result, e.g., lowering uric acid levels to a target goal or treating gout in its various forms or treating conditions associated with hyperuricemia.

"Treatment" and "treating" of a disease, disorder, condition or symptom refer to (1) preventing or reducing the risk of developing the disease, disorder or condition, i.e., causing the clinical symptoms of the disease, disorder or condition not to develop in a subject who may be exposed to or predisposed to the disease, disorder or condition but who does not yet experience or display symptoms of the disease, disorder or condition (i.e. prophylaxis); (2) inhibiting the disease, disorder or condition, i.e., arresting or reducing the development of the disease, disorder or condition or its clinical symptoms; and (3) relieving the disease, disorder or condition, i.e., causing regression, reversal, or amelioration of the disease, disorder or condition or reducing the number, frequency, duration or severity of its clinical symptoms. The term "management" may be used synonymously.

"Urate" refers to uric acid (7,9-dihydro-1H-purine-2,6,8 (3H)-trione) and ions and salts thereof.

This application describes compositions, kits and methods for the treatment of hyperuricemia, that is, for lowering serum uric acid levels. One aspect of the current disclosure relates to a composition comprising a first urate-lowering agent and a second urate-lowering agent, wherein said first urate-lowering agent is a compound of Formula (I)

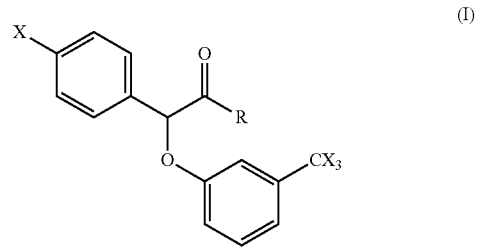

(I)

wherein R is selected from the group consisting of a hydroxy, lower aralkoxy, di-lower alkylamino-lower alkoxy, lower alkanamido-lower alkoxy, benzamido-lower alkoxy, ureido-lower alkoxy, N'-lower alkyl-ureido-lower alkoxy, carbamoyl-lower alkoxy, halophenoxy substituted lower alkoxy, carbamoyl substituted phenoxy, carbonyl-lower alkylamino, N,N-di-lower alkylamino-lower alkylamino, halo substituted lower alkylamino, hydroxy substituted lower alkylamino, lower alkanolyloxy substituted lower alkylamino, ureido, and lower alkoxycarbonylamino; and each X is independently a halogen; or a pharmaceutically acceptable salt thereof.

In certain aspects, the first urate-lowering agent is a compound of Formula (II)

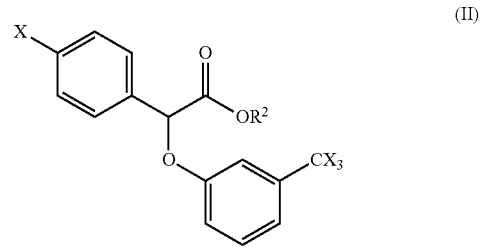

(II)

wherein $R^2$ is selected from the group consisting of phenyl-lower alkyl, lower alkanamido-lower alkyl, and benzamido-lower alkyl; and each X is independently a halogen, or a pharmaceutically acceptable salt thereof.

In other aspects, the first urate-lowering agent is a compound of Formula (III), also referred to as halofenate

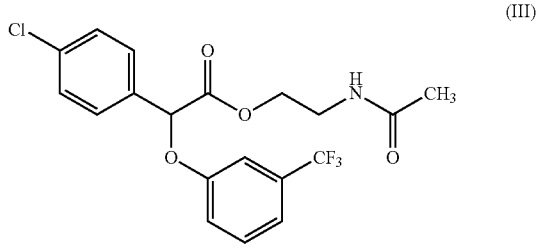 [SMILES: CC(=O)NCCOC(=O)C(Oc1cccc(C(F)(F)F)c1)c1ccc(Cl)cc1]

(III)

or a pharmaceutically acceptable salt thereof.

In other aspects, the first urate-lowering agent is a compound of Formula (IV), also referred to as halofenic acid

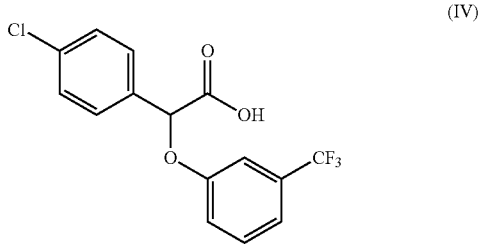 [SMILES: O=C(O)C(Oc1cccc(C(F)(F)F)c1)c1ccc(Cl)cc1]

(IV)

or a pharmaceutically acceptable salt thereof.

It should also be noted that any carbon atom with unsatisfied valences in the formulae and examples herein is assumed to have the hydrogen atom to satisfy the valences.

In certain embodiments the compound is a compound that generates the compound of Formula (IV) or a pharmaceutically acceptable salt thereof via a chemical reaction after being administered, as discussed in more detail below.

Another aspect provides for methods of treating a condition associated with an elevated serum uric acid level comprising administering to a subject in need thereof a pharmaceutical composition comprising a first urate-lowering agent, wherein said first urate-lowering agent is a compound of Formula (I), (II), (III) or (IV) or a pharmaceutically acceptable salt thereof; and a second urate-lowering agent. Another aspect provides a method of lowering the serum uric acid level in a subject comprising administering to a subject in need thereof a pharmaceutical composition comprising a first urate-lowering agent, wherein said first urate-lowering agent is a compound of Formula (I), (II), (III) or (IV) or a pharmaceutically acceptable salt thereof; and a second urate-lowering agent.

In certain embodiments, the first urate-lowering agent is (−)-halofenate (i.e. (−)-(R)-(4-chloro-phenyl)-(3-trifluoromethyl-phenoxy)-acetic acid 2-acetylamino-ethyl ester, also referred to as arhalofenate). In other embodiments, the first urate-lowering agent is (−)-halofenic acid (i.e. (−)-4-chlorophenyl-(3-trifluoromethylphenoxy) acetic acid) or a pharmaceutically acceptable salt thereof. In certain embodiments, the (−)-halofenate, (−)-halofenic acid, or pharmaceutically acceptable salt thereof is substantially free from the corresponding (+) enantiomer.

The enantiomers (stereoisomers) of compounds of Formula (I), (II), (III) or (IV) and pharmaceutically acceptable salt thereof can be prepared by using reactants or reagents or catalysts in their single enantiomeric form in the process wherever possible or by resolving the mixture of stereoisomers by conventional methods including use of microbial resolution, resolving the diastereomeric salts formed with chiral acids or chiral bases and chromatography using chiral supports. See, also U.S. Pat. No. 7,199,259 (Daugs), U.S. Pat. Nos. 6,646,004; 6,624,194; 6,613,802; and 6,262,118 (each to Luskey et al.), U.S. Pat. No. 7,714,131 (Zhu et al.), U.S. Pat. No. 7,432,394 (Cheng et al.) and U.S. Publication No. 2010/0093854 (Broggini et al.) each of which are incorporated herein by reference in their entireties.

The chemical synthesis of racemic mixtures of (3-trihalomethylphenoxy) (4-halophenyl) acetic acid derivatives can also be performed by the methods described in U.S. Pat. No. 3,517,050, the teachings of which are incorporated herein by reference. The individual enantiomers can be obtained by resolution of the racemic mixture of enantiomers using conventional means known to and used by those of skill in the art. See, e.g., Jaques, J., et al., in *Enantiomers, Racemates, and Resolutions*, John Wiley and Sons, New York (1981). Other standard methods of resolution known to those skilled in the art, including but not limited to, simple crystallization and chromatographic resolution, can also be used (see, e.g., *Stereochemistry of Carbon Compounds* (1962) E. L. Eliel, McGraw Hill; J. Lochmuller, *Chromatography*, 113, 283-302 (1975)). Additionally, halofenate, halofenic acid, or a pharmaceutically acceptable salt thereof, i.e., the optically pure isomers, can be prepared from the racemic mixture by enzymatic biocatalytic resolution. Enzymatic biocatalytic resolution has been generally described previously (see, e.g., U.S. Pat. Nos. 5,057,427 and 5,077,217, the disclosures of which are incorporated herein by reference). Other generic methods of obtaining enantiomers include stereospecific synthesis (see, e.g., A. J. Li et al., *Pharm. Sci.* 86, 1073-77 (1997).

One embodiment provides a composition comprising a pharmaceutically acceptable salt of halofenate or halofenic acid. The neutral forms of the therapeutic agents may be regenerated by contacting the salt with a base or acid and isolating the parent therapeutic agent in the conventional manner. The parent form of the therapeutic agent differs from the various salt forms in certain physical properties, such as solubility in polar solvents, but otherwise the salts are equivalent to the parent form.

The second urate-lowering agent may be any other agent (i.e. not a first urate-lowering agent, as defined herein) that lowers serum uric acid levels. These second urate-lowering agents include inhibitors of uric acid production (e.g. xanthine oxidase inhibitors and purine nucleoside phosphorylase inhibitors), uricosuric agents and uricases.

For example, in some embodiments, the second urate-lowering agent is a xanthine oxidase inhibitor. Xanthine oxidase inhibitors lower the amount of urate in blood by decreasing the synthesis of uric acid. Xanthine oxidase is involved in purine metabolism and inhibiting the enzyme reduces uric acid levels. Xanthine oxidase inhibitors include, but are not limited to: allopurinol, febuxostat, oxypurinol, tisopurine, an inositol and propolis. In some embodiments, the xanthine oxidase inhibitor is allopurinol, febuxostat, oxypurinol, tisopurine, inositol, phytic acid, myo-inositiol, kaempferol, myricetin, and quercetin. Allopurinol (1,5-dihydro-4H-pyrazolo[3,4-d]pyrimidin-4-one), a xanthine oxidase inhibitor, is the current first line standard of care for lowering urate levels. Another xanthine oxidase inhibitor, febuxostat (2-(3-cyano-4-isobutoxyphenyl)-4-methyl-1,3-thiazole-5-carboxylic acid), was approved for treatment of gout in February 2009. In one embodiment, halofenate, halofenic acid or a pharmaceutically acceptable salt thereof, is administered before, concurrently or subsequent to administration of allopurinol. In one embodiment, halofenate, halofenic acid or a pharmaceutically acceptable salt thereof is administered before, concurrently or subsequent to administration of febuxostat.

In other embodiments, the second urate-lowering agent is a purine nucleoside phosphorylase (PNP) inhibitor. Purine nucleoside phosphorylase inhibitors represent a relatively new approach to lowering serum uric acid levels in patient with hyperuricemia, gout, and related conditions. In some embodiments, the PNP inhibitor is forodesine (BCX1777) (BioCryst Pharmaceuticals, Inc.). In other embodiments, the PNP inhibitor is ulodesine (BCX4208; 7-(((3R,4R)-3-hydroxy-4-(hydroxymethyl)pyrrolidin-1-yl)methyl)-3H-pyrrolo[3,2-d]pyrimidin-4(5H)-one) (BioCryst Pharmaceuticals, Inc.). Ulodesine monotherapy administered at 40, 80, 120, 160 and 240 mg/day has been shown to rapidly and significantly reduced serum uric acid in gout patients.

In some embodiments, the second urate-lowering agent is a uricosuric agent. Uricosuric agents enhance renal excretion of uric acid and generally act by lowering the absorption of uric acid from the kidney proximal tubule back to the blood, e.g., by inhibiting urate transporters, e.g, SLC22A12. Uricosuric agents include, but are not limited to, probenecid, 2-((5-bromo-4-(4-cyclopropylnaphthalen-1-yl)-4H-1,2,4-triazol-3-yl)thio)acetic acid (RDEA594, lesinurad), potassium 4-(2-((5-bromo-4-(4-cyclopropylnaphthalen-1-yl)-4H-1,2,4-triazol-3-yl)thio)acetamido)-3-chlorobenzoate (RDEA806), RDEA684, benzbromarone, sulfinpyrazone, amlodipine, atorvastatin, fenofibrate, guaifenesin, losartan, adrenocorticotropic hormone, and cortisone. Probenecid is the most commonly used uricosuric agent in the U.S. and may be given in combination with allopurinol to some gout patients. Benzbromarone and sulfinpyrazone are also used as first line uricosuric agents. Guaifenesin, losartan, atorvastatin, amlodipine, adrenocorticotropic hormone (ACTH or corticotropin), fenofibrate, levotofisopam and cortisone also have uricosuric effects. In one embodiment, a first urate-lowering agent (e.g. (−)-halofenate, (−)-halofenic acid or a pharmaceutically acceptable salt thereof) is administered before, concurrently or subsequent to administration of a uricosuric agent. In one embodiment, a first urate-lowering agent (e.g. (−)-halofenate, (−)-halofenic acid or a pharmaceutically acceptable salt thereof) is administered before, concurrently or subsequent to administration of probenecid, benzbromarone or sulfinpyrazone.

In some embodiments, the second urate-lowering agent is a uricase enzyme, or a fragment or pegylated derivative thereof. Uricase or urate oxidase enzymes are found in many mammals but not in humans. They can lower uric acid levels by converting uric acid into allantoin, a benign end metabolite which is easily excreted in the urine. Uricase enzymes include, but are not limited to, rasburicase or a pegylated uricase enzyme (PEG-uricase). In some embodiments, the pegylated uricase enzyme is Krystexxa® (PURICASE®; pegloticase) (Savient Pharmaceuticals, Inc.) which is approved in the U.S. for the treatment of chronic gout in adult patients refractory to conventional therapy.

The present disclosure also provides for methods of treating one or more conditions associated with an elevated serum uric acid level, i.e. hyperuricemia, the methods comprising administering to a subject in need thereof a pharmaceutical composition comprising a first urate-lowering agent, wherein said first urate-lowering agent is a compound of Formulae (I), (II), (III) or (IV) or a pharmaceutically acceptable salt thereof; and a second urate-lowering agent. Conditions associated with hyperuricemia include, but are not limited to: gout; acute gout; chronic gout; moderate gout; refractory gout; severe gout; deposition of uric acid crystals in the urinary tract, renal parenchyma, soft tissues, joints, cartilage or bones; urolithiasis; urate nephropathy; tophi; podagra; acute inflammatory gouty arthritis; joint destruction; urinary tract infections; renal impairment; chronic kidney disease; kidney stones; local inflammation; systemic inflammation; immune-related disorders; cardiovascular disease including peripheral vascular disease, coronary artery disease and cerebrovascular disease; insulin resistance; diabetes; fatty liver disease; dementia including vascular dementia; dyslipidemia; preeclampsia; hypertension; obesity; muscle spasm; localized swelling; pain including joint pain, muscle fatigue; tumor-lysis syndrome; and stress feelings. Additional conditions associated with hyperuricemia include, but are not limited to, Lesch-Nyhan syndrome, Kelley-Seegmiller syndrome and related conditions.

A variety of factors increase the risk that a patient will have gout or will experience one or more of its symptoms. In addition to hyperuricemia, these factors include obesity, diabetes, chronic kidney failure, hypertension, use of diuretic drugs and certain other drugs (e.g. salicylates, pyrazinamide, ethambutol, nicotinic acid, cyclosporin, 2-ethylamino-1,3,4-thiadiazole, fructose and cytotoxic agents), overeating or fasting, a high purine diet, a high fructose diet, exposure to lead, consumption of red meat and protein, alcohol intake, and injury or recent surgery. Acute gout can be precipitated by perioperative ketosis in surgical patients, reduced body temperature, e.g., while sleeping, and by dehydration, e.g., by use of diuretic drugs. Genetic risk factors for gout and hyperuricemia have also been identified.

In various embodiments, the methods described herein may be used to treat any of the aforementioned conditions or disorders. That is, in one embodiment, the condition associated with an elevated serum uric acid level is gout. In some embodiments, the subject has acute gout. In some embodiments, the subject has chronic gout. In some embodiments the subject has moderate gout. In some embodiments the subject has refractory gout. For example, in some embodiments, a subject has been administered a second urate-lowering agent (e.g. allopurinol, febuxostat, probenecid, Krystexxa®, etc.) and has not been administered a first urate-lowering agent, and has been deemed to be poorly responsive or unresponsive as defined above (e.g. has failed to reach a target urate level (e.g. 6.0 mg/dL)). In some embodiments the subject has severe gout. For example, one method provides for the management of hyperuricemia in a subject with gout. Certain methods provide for the treatment or management of hyperuricemia in a subject with gout comprising administering a pharmaceutical composition comprising a first urate-lowering agent and a second urate-lowering agent. In some embodiments the first urate-lowering agent is (−)-halofenate, (−)-halofenic acid or a pharmaceutically acceptable salt thereof. In certain embodiments, the treatment can be for about four weeks or longer, for about one month or longer, for about 12 weeks or longer, for about three months or longer, for about six months or longer, for about one year or longer, for about two years or longer, for about five years or longer, for about 10 years or longer. In certain embodiments the treatment can be indefinite, e.g. for the remainder of the lifetime of the subject. In certain embodiments the second urate-lowering agent is selected from the group consisting of a uric acid synthesis inhibitor, a uricase, and a uricosuric agent, and pharmaceutically acceptable salts thereof. In certain embodiments the second agent may be allopurinol or febuxostat.

In various embodiments the methods comprise treating gout. In some embodiments, the methods comprise treating gout by preventing gout flares. In another embodiment the method comprises reducing the number, frequency, duration or severity of one of more gout flares. In another embodiment the method comprises preventing, reducing or reversing uric acid crystal formation. In some embodiments of the methods for treating uric acid crystal formation, the uric acid crystal formation is in one or more of the joints, under skin, and kidney. In some embodiments, the formations include tophaceous deposits. In some embodiments, the subject has uric acid crystal formation determined by aspiration of tophi or by aspiration of synovial fluid of an inflamed joint. In another embodiment the method comprises reducing uric acid burden. In another embodiment the method comprises reducing the size or number of tophi. The size or number of tophi may be assessed by known methods, for example, use of CT scans.

This application also provides methods of lowering the serum uric acid level, treating a subject having a condition associated with an elevated serum uric acid level, and treating hyperuricemia in a subject with gout, in subjects with refractory gout. In certain embodiments, the subject is refractory to allopurinol, 2-((5-bromo-4-(4-cyclopropyl-naphthalen-1-yl)-4H-1,2,4-triazol-3-yl)thio)acetic acid (RDEA594, lesinurad), 2-(3-cyano-4-isobutoxyphenyl)-4-methyl-1,3-thiazole-5-carboxylic acid (febuxostat), or ulodesine (BCX4208). In some embodiments the subject is refractory to allopurinol. For example, in one embodiment, the subject is refractory to allopurinol administered at from 100 mg/day to 800 mg/day (e.g. from 100 mg/day to 300 mg/day) for about one month or longer, about three months or longer, about one year or longer, etc. In some embodiments the subject is refractory to febuxostat. For example, in one embodiment the subject is refractory to febuxostat administered at from 40 mg/day to 120 mg/day for about one month or longer, about three months or longer, about one year or longer, etc. In certain embodiments the subject has mild or moderate chronic kidney disease (CKD2-3). In other embodiments the subject has severe chronic kidney disease (CKD4). In other embodiments, the subject is on aspirin or diuretic therapy.

It will be recognized by persons with ordinary skill in the art that patients with gout or at risk of developing gout may be administered agents such as non-steroidal anti-inflammatory drugs (NSAIDS), colchicine, steroids, or similar medicaments to treat or manage gout flares. Accordingly, in certain embodiments of the methods described herein, the subjects may also be administered an agent such as an NSAID, colchicine or a steroid.

The methods described herein may be accomplished by the administration of a compound that generates the compound of Formula (IV) or a salt thereof via a chemical reaction after being administered. Such compounds include prodrugs of the compound of Formula (IV). Prodrugs of a compound are prepared by modifying functional groups present in the compound in such a way that the modifications may be cleaved in vivo to release the parent compound, or an active metabolite. For example, prodrugs include compounds wherein a hydroxy, amino, or sulfhydryl group in a compound is bonded to any group that may be cleaved in vivo to regenerate the free hydroxyl, amino, or sulfhydryl group, respectively. Certain prodrugs may increase the bioavailability of the compounds of the embodiments when such compounds are administered to a subject (e.g., by allowing an orally administered compound to be more readily absorbed into the blood) or which enhance delivery of the parent compound to a certain organ or tissue (e.g., kidneys, adipose tissue, liver, muscles or joints) relative to the parent species. Prodrugs of the compound of Formula (IV) include esters, amides, and carbamates (e.g., N, N-dimethylaminocarbonyl) of the hydroxy functional group of the compound of Formula (IV). The compounds of Formulae (I), (II) and (III) are non-limiting examples of prodrugs of the compound of Formula (IV). Further examples of prodrugs can be found in J. Rautio et al. *Prodrugs: design and clinical applications*, Nat. Rev. Drug Discov., 7, 255-270 (2008); Edward B. Roche, ed., *Bioreversible Carriers in Drug Design*, American Pharmaceutical Association and Pergamon Press, (1987); and T. Higuchi and V. Stella, *Pro-drugs as Novel Delivery Systems*, Vol. 14 of the A.C.S. Symposium Series (1975), each of which are hereby incorporated by reference herein.

In various embodiments, the compositions, methods, and kits described herein lower serum uric acid levels in a subject by about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or more, as compared to serum uric acid levels in the subject prior to administering the methods described herein. In various embodiments, serum uric acid levels are decreased about 5% to about 50%, decreased by about 25% to about 75%, or decreased by about 50% to about 99%. Methods to determine serum uric acid levels are well known in the art and are often measured as part of a standard chemistry panel of blood serum samples.

In some embodiments, the compositions, methods, and kits of the present disclosure lower serum uric acid levels in a subject to about 7 mg/dL or less, to about 6.8 mg/dL or less, to about 6 mg/dL or less, to about 5 mg/dL or less, to about 4 mg/dL or less, or to about 3 mg/dL or less as compared to serum uric acid levels in the subject prior to administering the methods or compositions described herein. In some embodiments, the methods of the present disclosure lower serum uric acid levels in a subject by 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10.0 mg/dL, or greater, as compared to serum uric acid levels in the subject prior to administering the methods or compositions described herein. In further embodiments, the methods described herein lower serum uric acid levels by between 0.1 and 10.0 mg/dL, between 0.5 and 6.0 mg/dL, between 1.0 and 4.0 mg/dL or between 1.5 and 2.5 mg/dL. The appropriate serum uric acid level may vary depending on the subject, and may vary for a given subject over time, depending upon the subject's overall medical condition. Similarly, the appropriate serum uric acid level for one group of subjects sharing a common medical condition may be different from that which is appropriate for a different group of subjects sharing a different medical condition. Thus, it may be advisable to reduce the serum uric acid level of a given group of subjects to, for example, below about 5 mg/dL, and to reduce the serum uric acid level of a different group of subjects to, for example, below about 4 mg/dL. In certain embodiments, the methods of the present disclosure decrease a serum uric acid level in the subject by an amount sufficient to result in the disappearance, reduction, amelioration, or the prevention of the onset, of one or more conditions associated with elevated serum uric acid over a certain timeframe, for example about four weeks or longer, about one month or longer, about three months or longer, about one year or longer, about two years or longer, etc. For example, a method can decrease the serum uric acid level in a subject by an amount sufficient to result in the disappearance or reduction of tophi over about four weeks or longer, about one month or longer, about three months or longer, about one year or longer, about two years or longer, etc.

In further embodiments, the methods of the present disclosure comprise administering a pharmaceutical composition comprising a first urate-lowering agent and a second therapeutic agent, as described herein, to a subject whose serum uric acid level is at least about 4 mg/dL, at least about 5 mg/dL, at least about 6 mg/dL, at least about 6.8 mg/dL, at least about 7 mg/dL, at least about 8 mg/dL, at least about 9 mg/dL, at least about 10 mg/dL, or at least about 11 mg/dL. Again, the amount of decrease of serum uric acid level that is appropriate may vary depending on the subject, depending upon the subject's overall medical condition. Similarly, the amount of decrease of serum uric acid level that is appropriate for one group of subjects sharing a common medical condition may be different from that which is appropriate for a different group of subjects sharing a different medical condition.

The therapeutic agents and combinations thereof disclosed herein are contemplated to exhibit therapeutic activity when administered in an amount which can depend on the particular case. The variation in amount can depend, for example, on the subject being treated and the active ingredients chosen. A broad range of doses can be applicable. Dosage regimes may be adjusted to provide the optimum therapeutic response. For example, several divided doses may be administered daily, weekly, monthly or other at suitable time intervals or the dose may be proportionally reduced as indicated by the exigencies of the situation. Such dosages are optionally altered depending on a number of variables, not limited to the activity of the one or more active ingredients used, the disease or condition to be treated, the mode of administration, the requirements of the individual subject, the severity of the disease or condition being treated, and the judgment of the practitioner.

As described throughout, the present disclosure contemplates combination therapy and methods of concomitant administration of a first and second urate-lowering agent (wherein these first and second urate-lowering agents are described above). Combination therapy and concomitant administration refer to the administration of the two agents (i.e., a first agent and a second urate-lowering agent, as described above) in any manner in which the pharmacological effects of both are manifested in the subject at the same time. Thus, such administration does not require that a single pharmaceutical composition, the same type of formulation, the same dosage form, or even the same route of administration be used for administration of both the first and second urate-lowering agents, or that the two agents be administered at the same time. Such administration may be accomplished most conveniently by the same dosage form and the same route of administration, at substantially the same time. For example, a first urate-lowering agent, e.g. halofenate, halofenic acid, or a pharmaceutically acceptable salt thereof, and a second urate-lowering agent, e.g. xanthine oxidase inhibitor (e.g., allopurinol or febuxostat), can be administered to the human subject together in a single oral dosage composition, such as a tablet or capsule, or each agent can be administered in separate oral dosage formulations. One advantage with separate formulations is an added flexibility in dosing, i.e. the dosage of the first and second urate-lowering agents can be changed independently, quickly, and easily. Where separate dosage formulations are used, the first and second urate-lowering agents can be administered at essentially the same time (i.e., simultaneously or concurrently), or at separately staggered times (i.e., sequentially).

Depending on factors such as the diagnosis, symptoms, and therapeutic goals of a particular subject, a wide range of dosages of the first and second agent can be contemplated. In various embodiments, the first urate-lowering agents may be administered from about 10 mg to about 1000 mg per day and the second urate-lowering agent may be administered from about 10 mg to about 4000 mg per day. For example, halofenate, halofenic acid, or a pharmaceutically acceptable salt thereof may be administered at about 100 mg/day, about 200 mg/day, about 300 mg/day, about 400 mg/day, about 500 mg/day, about 600 mg/day, about 700 mg/day, about 800 mg/day, about 900 mg/day, or about 1000 mg/day.

As described above, in certain embodiments the second agent is allopurinol. By way of non-limiting example, the currently recommended daily dosage of allopurinol is from 100 mg/day to 800 mg/day in increments of 100 mg/day. When administered as a second urate-lowering agent as described herein (i.e. when a first urate-lowering agent is also administered), the dosage range of allopurinol may be within, above, or below the currently recommended daily dosage, as provided above and as appropriate for the subject being treated. By way of non-limiting example, in certain embodiments wherein the first urate-lowering agent is arhalofenate (i.e. (−)-halofenate) and wherein the second urate-lowering agent is allopurinol, the following daily dosages may be administered: arhalofenate 100 mg/day, allopurinol 50 mg/day; arhalofenate 100 mg/day, allopurinol 100 mg/day; arhalofenate 100 mg/day, allopurinol 200 mg/day; arhalofenate 100 mg/day, allopurinol 300 mg/day; arhalofenate 100 mg/day, allopurinol 400 mg/day; arhalofenate 100 mg/day, allopurinol 600 mg/day; arhalofenate 100 mg/day, allopurinol 800 mg/day; arhalofenate 200 mg/day, allopurinol 50 mg/day; arhalofenate 200 mg/day, allopurinol 100 mg/day; arhalofenate 200 mg/day, allopurinol 200 mg/day; arhalofenate 200 mg/day, allopurinol 300 mg/day; arhalofenate 200 mg/day, allopurinol 400 mg/day; arhalofenate 200 mg/day, allopurinol 600 mg/day; arhalofenate 200 mg/day, allopurinol 800 mg/day; arhalofenate 300 mg/day, allopurinol 50 mg/day; arhalofenate 300 mg/day, allopurinol 100 mg/day; arhalofenate 300 mg/day, allopurinol 200 mg/day; arhalofenate 300 mg/day, allopurinol 300 mg/day; arhalofenate 300 mg/day, allopurinol 400 mg/day; arhalofenate 300 mg/day, allopurinol 600 mg/day; arhalofenate 300 mg/day, allopurinol 800 mg/day; arhalofenate 400 mg/day, allopurinol 50 mg/day; arhalofenate 400 mg/day, allopurinol 100 mg/day; arhalofenate 400 mg/day, allopurinol 200 mg/day; arhalofenate 400 mg/day, allopurinol 300 mg/day; arhalofenate 400 mg/day, allopurinol 400 mg/day; arhalofenate 400 mg/day, allopurinol 600 mg/day; arhalofenate 400 mg/day, allopurinol 800 mg/day; arhalofenate 600 mg/day, allopurinol 50 mg/day; arhalofenate 600 mg/day, allopurinol 100 mg/day; arhalofenate 600 mg/day, allopurinol 200 mg/day; arhalofenate 600 mg/day, allopurinol 300 mg/day; arhalofenate 600 mg/day, allopurinol 400 mg/day; arhalofenate 600 mg/day, allopurinol 600 mg/day; arhalofenate 600 mg/day, allopurinol 800 mg/day; arhalofenate 800 mg/day, allopurinol 50 mg/day; arhalofenate 800 mg/day, allopurinol 100 mg/day; arhalofenate 800 mg/day, allopurinol 200 mg/day; arhalofenate 800 mg/day, allopurinol 300 mg/day, allopurinol 400 mg/day; arhalofenate 800 mg/day, allopurinol 600 mg/day; arhalofenate 800 mg/day, allopurinol 800 mg/day.

Also as described above, in certain embodiments the second agent is febuxostat. By way of non-limiting example, the currently recommended daily dosage of febuxostat is 40 mg/day or 80 mg/day in the United States, and 10 mg/day, 40 mg/day, 80 mg/day or 120 mg/day in certain other countries. When administered as a second urate-lowering agent as described herein (i.e. when a first urate-lowering agent is also administered), the dosage range of febuxostat may be within, above, or below the currently recommended daily dosage, as provided above and as appropriate for the subject being treated. By way of non-limiting example, in certain embodiments wherein the first urate-lowering agent is arhalofenate (i.e. (−)-halofenate) and wherein the second urate-lowering agent is febuxostat, the following daily dosages may be administered: arhalofenate 100 mg/day, febuxostat 10 mg/day; arhalofenate 100 mg/day, febuxostat 40 mg/day; arhalofenate 100 mg/day, febuxostat 80 mg/day; arhalofenate 100 mg/day, febuxostat 120 mg/day; arhalofenate 100 mg/day, febuxostat 240 mg/day; arhalofenate 200 mg/day, febuxostat 10 mg/day; arhalofenate 200 mg/day, febuxostat 40 mg/day; arhalofenate 200 mg/day, febuxostat 80 mg/day; arhalofenate 200 mg/day, febuxostat 120 mg/day; arhalofenate 200 mg/day, febuxostat 240 mg/day; arhalofenate 300 mg/day, febuxostat 10 mg/day; arhalofenate 300 mg/day, febuxostat 40 mg/day; arhalofenate 300 mg/day, febuxostat 80 mg/day; arhalofenate 300 mg/day, febuxostat 120 mg/day; arhalofenate 300 mg/day, febuxostat 240 mg/day; arhalofenate 400 mg/day, febuxostat 10 mg/day; arhalofenate 400 mg/day, febuxostat 40 mg/day; arhalofenate 400 mg/day, febuxostat 80 mg/day; arhalofenate 400 mg/day, febuxostat 120 mg/day; arhalofenate 400 mg/day, febuxostat 240 mg/day; arhalofenate 600 mg/day, febuxostat 10 mg/day; arhalofenate 600 mg/day, febuxostat 40 mg/day; arhalofenate 600 mg/day, febuxostat 80 mg/day; arhalofenate 600 mg/day, febuxostat 120 mg/day; arhalofenate 600 mg/day, febuxostat 240 mg/day; arhalofenate 800 mg/day, febuxostat 10 mg/day; arhalofenate 800 mg/day, febuxostat 40 mg/day; arhalofenate 800 mg/day, febuxostat 80 mg/day; arhalofenate 800 mg/day, febuxostat 120 mg/day; and arhalofenate 800 mg/day, febuxostat 240 mg/day.

Other dose ranges within the ranges described for each of the first urate-lowering agent and the second urate-lowering agent may be readily envisaged. One of skill in the art will appreciate that the dose and dosing regimen may be adjusted when therapeutic agents are used in combination. When such combinations are used, the dose of one or more of the agents may be reduced to a level below the level required for a desired efficacy when the one or more agents are used alone. Similarly, the dosing regimen may be modified, e.g., to synchronize the dosing of the one or more therapeutic agents to facilitate improved patient ease of use and compliance. Alternately, the dosing regimen of the one or more therapeutic agents can be sequential, e.g., to reduce the combined load of the agents at a given time. For example, in certain embodiments, the dose of the second urate-lowering agent (e.g. allopurinol, febuxostat, or the other second urate-lowering agents described herein) can be adjusted to a lower level than that currently recommended when the first urate-lowering agent is and second urate-lowering agents are administered.

In certain embodiments, the concomitant administration of a first urate-lowering agent and a second urate-lowering agent provides an additive effect or a over-additive effect. As used herein, the term "additive effect" refers to the combined effect of two or more pharmaceutically active agents that is approximately equal to the sum of the effect of each agent given alone, and the term "over-additive effect" refers to the combined effect of two or more pharmaceutically active agents that is greater than the sum of the effect of each agent given alone. For example, in some embodiments, the concomitant administration of a first urate-lowering agent and a second urate-lowering agent provides an additive lowering of serum uric acid in a subject. In some embodiments, the concomitant administration of a first urate-lowering agent and a second urate-lowering agent provides an additive or over-additive lowering of serum uric acid in a subject. For example, the concomitant administration of (−)-halofenate and febuxostat may provide an additive or over-additive lowering of serum uric acid. In certain embodiments, the first urate-lowering agent and the second urate-lowering agent are compatible. As used herein, the term "compatible" means that no clinically significant adverse drug-drug interaction occurs. By way of non-limiting example, an adverse drug-drug interaction could manifest as a lower plasma concentration of a second urate-lowering agent or its metabolite when a first urate-lowering agent and a second urate-lowering agent are concomitantly administered as compared to the corresponding concentration when administered without the other agent and at the same dosage.

Dose titration or dose escalation protocols may be employed to determine the proper or optimal dose to administer to a subject. For example, dose titration or escalation studies may select for doses that improve efficacy or tolerability. Dose titration or escalation allows for the gradual adjusting of the dose administered until the desired effect is achieved. Dose titration gradually decreases the dosage administered while dose escalation gradually increases the dose administered. Methods of dose titration and escalation are well known in the art. As a non-limiting example, a subject may be administered 600 mg/day (−)-halofenate, (−)-halofenic acid, or a pharmaceutically acceptable salt thereof every day and measured for serum uric acid levels on a daily basis. The dosage may be increased or decreased, for example, on a weekly basis. The subject may be monitored for a period of, for example, 2 to 12 weeks to find the desired dose.

In accordance with the compositions, methods and kits described herein, the first urate-lowering agent and second urate-lowering agent may be administered in any manner in which the pharmacological effects of both are likely to be manifested in the subject at approximately the same time. Such administration does not require that a single pharmaceutical composition, the same type of formulation, the same dosage form, or even the same route of administration be used for administration of both the first and second urate-lowering agents, or that the two agents be administered at the same time. That is, in various embodiments, the first urate-lowering agent and the second urate-lowering agent described herein may be present in a single dosage form (e.g. a single tablet or capsule for oral administration), and in other embodiments the first urate-lowering agent may be present in a first dosage form (e.g. a first tablet or capsule) and the second urate-lowering agent may be present in a second dosage form (e.g. a second tablet or capsule). The dosage forms may include the first and second urate-lowering agents in doses according to the examples provided above. A single dosage form (e.g a single tablet or capsule) may include a single daily supply of the first and second urate-lowering agent, or a fraction thereof, e.g. one-half of a daily supply, one-third a daily supply, one-fourth a daily supply, etc. For example, the pharmaceutical composition described herein can be in a single tablet comprising 600 mg of arhalofenate and 150 mg of allopurinol. By way of further example, the pharmaceutical composition described herein can be in a single tablet comprising 800 mg of arhalofenate and 40 mg of febuxostat. Other dosage forms within the scope of this disclosure may be readily envisaged.

In unit dosage form, the formulation may be divided into unit doses containing appropriate quantities of the one or more active ingredients. In some embodiments, the unit dosage is in the form of a package containing discrete quantities of the formulation. Non-limiting examples include packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative. Tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain one or more active ingredients, sucrose as a sweetening agent, methyl and propylparabens as preservatives, a dye and flavoring such as cherry or orange flavor. In some embodiments, additional ingredients, for example, nonsteroidal anti-inflammatory drugs or colchicine, ingredients for treating other related indications, or inert substances such as artificial coloring agents are added. Of course, any material used in preparing any dosage unit form should be pharmaceutically pure and substantially non-toxic in the amounts employed. In addition, the one or more active ingredients may be incorporated into sustained-release preparations and formulations as described herein.

The pharmaceutical compositions of the present disclosure may be administered once daily (QD), twice daily (BID), three times daily (TID) or four times per day (QID). In one embodiment, the pharmaceutical composition of the present disclosure is administered once daily (QD). In another embodiment, the pharmaceutical composition of the present disclosure is administered twice daily (BID).

This disclosure also describes articles of manufacture such as kits comprising a composition comprising a first and second urate-lowering agent (wherein these first and second urate-lowering agents are described above). In some embodiments the first urate-lowering agent in the kit is (−)-halofenate (i.e. arhalofenate). In some embodiments the second urate-lowering agent in the kit is allopurinol. In other embodiments the second urate-lowering agent in the kit is febuxostat. The kits can include the compositions packaged for distribution and in quantities sufficient to carry out the methods described herein. Kits may also include instructions (e.g. a package insert, package label, etc.) for using the kit components in one or more methods described herein. For example, a kit may comprise dosage forms of a first urate-lowering agent and a second urate-lowering agent described herein, and instructions for prescribing, administering or otherwise using the dosage forms to lower serum uric acid levels. In some embodiments a kit is for a subject with hyperuricemia or a condition associated with hyperuricemia (e.g., gout) to use in the self-administration of the pharmaceutical composition, wherein the kit comprises a container housing a plurality of dosage forms containing a first and second urate-lowering agent described herein and instructions for carrying out drug administration therewith. In one embodiment, a kit comprises a first dosage form comprising halofenate, halofenic acid, or a pharmaceutically acceptable salt thereof in one or more of the forms identified above and at least a second dosage form comprising one or more of the forms identified above, in quantities sufficient to carry out the methods of the present disclosure. The second dosage form, and any additional dosage forms (e.g., a third, fourth of fifth dosage form) can comprise any active ingredient disclosed herein for the treatment of a hyperuricemic disorder (e.g., gout). All dosage forms together can comprise a therapeutically effective amount of each compound for the treatment of a condition associated with hyperuricemia (e.g., gout). In some embodiments a kit is for a subject with a condition associated with hyperuricemia (e.g., gout) to use in the self-administration of at least one oral agent, wherein the kit comprises a container housing a plurality of said oral agents and instructions for carrying out drug administration therewith.

EXAMPLES

Example 1

Clinical Trial

A randomized, double-blind, placebo-controlled study to evaluate the safety and efficacy of daily oral doses of between 400 to 600 mg of arhalofenate (i.e., (−)-halofenate) in combination with 300 mg oral doses of allopurinol was conducted in gout patients with inadequate hypouricemic (uric acid lowering) response to allopurinol alone. A subset of enrolled patients volunteered to participate in the allopurinol/oxypurinol serial PK sample collection sub-study.

Patients who met the final eligibility criteria were randomized to each of 3 study arms in the following manner (1:1:1):

Arhalofenate 400 mg (plus allopurinol 300 mg)
Arhalofenate 600 mg (plus allopurinol 300 mg)
Placebo (plus allopurinol 300 mg)

The serum uric acid (sUA) levels were assessed at Day 1, prior to giving blinded study medication, and at Visits Week 2, 3, and 4.

Dose/Route/Regimen:

Colchicine at 0.6 mg was administered once daily orally to patients in all treatment groups starting at Week −3 through the final study follow-up visit, as background therapy for prophylaxis of gout flares. Patients in all treatment groups also took allopurinol 300 mg once daily orally starting at Week −3 during the run-in and continuing through Week 4.

The randomized treatment regimens were as follows (Day 1 through Week 4):

Treatment Group #1: Arhalofenate 400 mg (plus allopurinol)
Treatment Group #2: Arhalofenate 600 mg (plus allopurinol)
Treatment Group #3: Placebo (plus allopurinol)

Safety

The interpretation of the safety and tolerability of allopurinol-arhalofenate combination treatment was made based on the assessment of safety parameters evaluated throughout the study, including clinical laboratory tests, 12-lead ECGs, vital signs, physical examination, concomitant medication review, and treatment emergent adverse events (AEs). The reporting of the safety data was descriptive, and included all patients receiving at least one dose of arhalofenate or allopurinol.

Pharmacodynamics

The effects of each of the three treatment groups were assessed as the change in sUA from baseline to the end of the treatment period for the following endpoints:

Percent change in sUA from baseline at Week 4 of treatment

The proportion of patients achieving a sUA <6 mg/dL at week 4 of treatment

The proportion of patients achieving a sUA <5 mg/dL at week 4 of treatment

The proportion of patients achieving a sUA <4 mg/dL at week 4 of treatment

Results:

A total of 100 patients were randomized and received at least one dose of double-blind study medication: 33 received 300 mg allopurinol plus placebo, 35 received 400 mg arhalofenate plus 300 mg allopurinol, and 32 received 600 mg arhalofenate plus 300 mg allopurinol. Patients who received at least one dose of double-blind study medication are included in the safety analysis.

At Week 4, after four weeks of daily treatment with blinded study drug, the mean percent sUA change from baseline were statistically significant in all treatment groups: −9.5% in Placebo plus Allopurinol 300 mg group (p=0.0090), −16.0% in Arhalofenate 400 mg plus Allopurinol 300 mg group (p<0.0001), and −9.9% in arhalofenate 600 mg plus Allopurinol 300 mg group (p=0.0037). No statistically significant differences were seen when comparing the arhalofenate+allopurinol treated groups with placebo+allopurinol group.

TABLE 1

Summary and Analysis of Percent Changes from Baseline in Uric Acid (mg/dL) at the End of Treatment

|  | Placebo + Allopurinol (N = 31) | 400 mg Arhalofenate + Allopurinol (N = 34) | 600 mg Arhalofenate + Allopurinol (N = 30) |
|---|---|---|---|
| Baseline[1] | | | |
| n | 31 | 34 | 30 |
| Mean (SD) | 7.1 (1.0) | 7.3 (1.1) | 7.1 (1.1) |
| SEM | 0.2 | 0.2 | 0.2 |
| Median | 6.8 | 7.1 | 6.8 |
| Minimum, maximum | 6.0, 9.9 | 6.0, 9.9 | 6.0 11.2 |
| End of Treatment (LOCF) | | | |
| n | 31 | 34 | 30 |
| Mean (SD) | 6.3 (1.1) | 6.1 (1.5) | 6.4 (1.3) |
| SEM | 0.2 | 0.3 | 0.2 |
| Median | 6.2 | 5.9 | 6.0 |
| Minimum, maximum | 3.9, 8.4 | 3.4, 10.1 | 4.3, 8.8 |
| % Change from Baseline | | | |
| Mean (SD) | −9.5 (19.0) | −16.0 (20.9) | −9.9 (17.1) |
| SEM | 3.4 | 3.6 | 3.1 |
| Median | −8.7 | −18.8 | −8.8 |
| Minimum, maximum | −57.6, 27.3 | −46.0, 56.5 | −46.4, 41.9 |
| P-value for within Group Change | | | |
|  | 0.0090[2] | <0.0001[3] | 0.0037[2] |
| P-value for Change from Baseline[4] | | | |
| Arhalofenate vs placebo | | 0.1956 | 0.9415 |
| 600 mg vs 400 mg | | | 0.2053 |
| Mean Difference CI (Treatment - allopurinol alone) | | (−16.5, 3.4) | (−9.6, 8.9) |

By the End of Treatment (Week 4), 11 patients in the placebo+allopurinol 300 mg group, 18 patients in the arhalofenate 400 mg+allopurinol 300 mg group and 13 patients in the arhalofenate 600 mg+allopurinol 300 mg group had sUA <6.0 mg/dL; 4 patients in the placebo+allopurinol 300 mg group, 8 patients in the arhalofenate 400 mg+allopurinol 300 mg group and 4 patients in the arhalofenate 600 mg+allopurinol 300 mg group had sUA <5.0 mg/dL; and 1 patients in the placebo+allopurinol 300 mg group, and 1 patients in the arhalofenate 400 mg+allopurinol 300 mg group had sUA <4.0 mg/dL. No statistically significant differences were seen between the arhalofenate+allopurinol groups and the placebo+allopurinol group.

Example 2

Clinical Trial

This study evaluated the efficacy, safety and tolerability of arhalofenate at 400 mg increasing to 600 mg daily orally in combination with febuxostat 80 mg daily orally in gout patients (per criteria of the American Rheumatism Association) with hyperuricemia.

In addition to colchicine 0.6 mg daily for flare prophylaxis, all patients received febuxostat and arhalofenate in the following order during the Treatment Phase:

Days 1 through 7: febuxostat 80 mg orally once daily (febuxostat only period)

Days 8 through 21: febuxostat 80 mg plus arhalofenate 400 mg orally once daily (febuxostat plus arhalofenate 400 mg period)

Days 22 through 35: febuxostat 80 mg plus arhalofenate 600 mg orally once daily (febuxostat plus arhalofenate 600 mg period)

The sUA levels were assessed before the start of each dosing period (Day 1, Day 8, Day 22) and at the end of the Treatment Phase (Day 36). Serum urate levels were also measured on the last day of each dosing period (Day 7, Day 21, and Day 35) at 4 different time points; pre-dose (fasting), 2 hours post-dose, 6 hours post-dose, and 10 hours post-dose.

Dose/Route/Regimen

Colchicine: 0.6 mg/oral/daily from Day −16 through Day 49

Febuxostat: 80 mg/oral/daily from Day 1 through Day 35

Arhalofenate: 400 mg/oral daily from Day 8 through Day 21; 600 mg/oral/daily from Day 22 through Day 35

Duration of Treatment

Phase 1: Screening Phase: 1 to 4 weeks
Phase 2: Run-in/Stabilization Phase: >2 weeks
Phase 3: Treatment Phase: 5 weeks
Phase 4: Follow-up Phase: 2 weeks
Safety The interpretation of the safety and tolerability was made based on the assessment of safety parameters evaluated throughout the study, including clinical laboratory tests, 12-lead ECGs, vital signs, physical examination, concomitant medication review, and treatment emergent AEs. The reporting of the safety data was descriptive, and included all patients receiving at least one dose of arhalofenate.

Pharmacodynamics

The effects of each of the febuxostat plus arhalofenate combination treatment periods was assessed as the change in sUA from baseline (Day 1) to end of treatment period for the following endpoints:

The proportion of patients achieving a sUA <6 mg/dL at Day 22 and Day 36

The proportion of patients achieving a sUA <5 mg/dL at Day 22 and Day 36

The proportion of patients achieving a sUA <4 mg/dL at Day 22 and Day 36

The proportion of patients achieving a sUA <3 mg/dL at Day 22 and Day 36

Absolute and percent change in sUA at Day 22 and Day 36

Results:

A total of 12 patients met the final eligibility criteria and took the 1st dose of febuxostat 80 mg on Day 1. A total of 11 patients participated in the arhalofenate-febuxostat periods and completed the entire study.

At Day 8, after one week of daily treatment with 80 mg febuxostat, 11 patients (100%) reached sUA target of <6 mg/dL, 6 patients (55%) reached <5 mg/dL, and 1 patient (9%) reached <4 mg/dL. At Day 22, after 2 weeks of daily treatment with 80 mg febuxostat plus 400 mg arhalofenate (preceded by 80 mg febuxostat daily for 1 week), statistically significantly higher proportion of patients achieved sUA target of <5 mg/dL compared with Day 8 (sUA <5.0 mg/dL in 10 patients, p=0.0455). By Day 36, after 2 weeks of daily treatment with 80 mg febuxostat plus 600 mg arhalofenate (preceded by 80 mg febuxostat daily for 1 week and 80 mg febuxostat plus 400 mg arhalofenate for 2 weeks), statistically significantly higher proportion of patients achieved sUA targets of <5 mg/dL and <4 mg/dL compared with Day 8 (sUA <5.0 mg/dL in 11 patients, p=0.0253; sUA <4.0 mg/dL in 7 patients, p=0.0143).

TABLE 2

Summary of Patients Reaching Target

| | Patients reached target: No | Patients reached target: Yes | Proportion of patients reached target | P-value (vs. Day 8) |
|---|---|---|---|---|
| sUA < 6.0 mg/dL | 0 | 11 | 100.00 | |
| sUA < 5.0 mg/dL | 5 | 6 | 54.55 | |
| sUA < 4.0 mg/dL | 10 | 1 | 9.09 | |
| sUA < 3.0 mg/dL | 11 | 0 | 0.00 | |
| sUA < 6.0 mg/dL | 0 | 11 | 100.00 | • |
| sUA < 5.0 mg/dL | 1 | 10 | 90.91 | 0.0455 |
| sUA < 4.0 mg/dL | 8 | 3 | 27.27 | 0.1573 |
| sUA < 3.0 mg/dL | 10 | 1 | 9.09 | 0.3173 |
| sUA < 6.0 mg/dL | 0 | 11 | 100.00 | • |
| sUA < 5.0 mg/dL | 0 | 11 | 100.00 | 0.0253 |
| sUA < 4.0 mg/dL | 4 | 7 | 63.64 | 0.0143 |
| sUA < 3.0 mg/dL | 9 | 2 | 18.18 | 0.1573 |

The mean percent (and absolute) reductions in sUA at Day 8, Day 22 and Day 36 from Day 1 were −47.8% (−4.3 mg/dL), −53.5% (−4.8 mg/dL), and −60.4% (−5.5 mg/dL), respectively. When comparing Day 8, Day 22 or Day 36 mean sUA values with Day 1 values, all of the mean absolute changes and mean percent changes in sUA were statistically significant (p<0.0001). At Day 22 and Day 36, the mean percent (and absolute) reductions in sUA from Day 8 were −11.0% (−0.5 mg/dL), and −24.4% (−1.1 mg/dL), respectively. When comparing Day 22 or Day 36 mean sUA values with Day 8 values, all of the mean absolute changes and mean percent changes in sUA were statistically significant (p<0.0001 for all except, p=0.0001 for percent change at Day 22).

No clinically meaningful differences were observed among the study treatments in adverse events, clinical laboratory test results, vital signs, ECG overall impression, or physical examination results.

While the foregoing description describes specific embodiments, those with ordinary skill in the art will appreciate that various modifications and alternatives can be developed. Accordingly, the particular embodiments and examples described above are meant to be illustrative only, and not to limit the scope of the invention, which is to be given the full breadth of the appended claims, and any and all equivalents thereof.

What is claimed is:

1. A method of treating hyperuricemia in a subject with gout, comprising concomitant administration to the subject of a therapeutically effective amount of a first urate-lowering agent that is (−)-halofenate, or (−)-halofenic acid or a pharmaceutically acceptable salt thereof, substantially free from its (+)-enantiomer, and a second urate-lowering agent that is febuxostat.

2. The method of claim 1, where the first urate-lowering agent is (−)-halofenate.

3. The method of claim 1, where the first urate-lowering agent is administered at between about 100 mg/day and about 1000 mg/day.

4. The method of claim 1, where the febuxostat is administered at between about 10 mg/day and about 240 mg/day.

5. The method of claim 2, where the (−)-halofenate is administered at between about 400 mg/day and about 800 mg/day and the febuxostat is administered at between about 40 mg/day and about 120 mg/day.

6. The method of claim 1, where the subject is refractory to febuxostat.

7. The method of claim 1, where the gout is severe gout.

8. The method of claim 1, where the gout is refractory gout.

9. A method of lowering serum uric acid in a subject with gout, comprising concomitant administration to the subject of a therapeutically effective amount of a first urate-lowering agent that is (−)-halofenate, or (−)-halofenic acid or a pharmaceutically acceptable salt thereof, substantially free from its (+)-enantiomer, and a second urate-lowering agent that is febuxostat.

10. The method of claim 9, where the first urate-lowering agent is (−)-halofenate.

11. The method of claim 9, where the first urate-lowering agent is administered at between about 100 mg/day and about 1000 mg/day.

12. The method of claim 9, where the febuxostat is administered at between about 10 mg/day and about 240 mg/day.

13. The method of claim 10, where the (−)-halofenate is administered at between about 400 mg/day and about 800 mg/day and the febuxostat is administered at between about 40 mg/day and about 120 mg/day.

14. The method of claim 9, where the subject is refractory to febuxostat.

15. The method of claim 9, where the gout is severe gout.

16. The method of claim 9, where the gout is refractory gout.

* * * * *